United States Patent
Wood et al.

(10) Patent No.: US 11,156,605 B2
(45) Date of Patent: *Oct. 26, 2021

(54) CAPTURE LIGAND CONTROLS, BLOCKING PROBES, MASKING PROBES AND METHODS OF USING THE SAME

(71) Applicant: GenMark Diagnostics, Inc., Carlsbad, CA (US)

(72) Inventors: Michael Leonard Wood, Danville, CA (US); Aviva Ruth Jacobs, Los Angeles, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/861,141

(22) Filed: Apr. 28, 2020

(65) Prior Publication Data

US 2020/0300846 A1 Sep. 24, 2020

Related U.S. Application Data

(63) Continuation of application No. 15/974,605, filed on May 8, 2018, now Pat. No. 10,670,591, which is a continuation of application No. 12/914,257, filed on Oct. 28, 2010, now Pat. No. 10,001,476.

(60) Provisional application No. 61/255,713, filed on Oct. 28, 2009.

(51) Int. Cl.
*G01N 33/543* (2006.01)
*C40B 40/04* (2006.01)

(52) U.S. Cl.
CPC ....... *G01N 33/54306* (2013.01); *C40B 40/04* (2013.01); *G01N 33/54393* (2013.01); *C12Q 2563/113* (2013.01); *C12Q 2565/607* (2013.01)

(58) Field of Classification Search
None
See application file for complete search history.

(56) References Cited

U.S. PATENT DOCUMENTS

| | | |
|---|---|---|
| 6,071,699 A | 6/2000 | Meade et al. |
| 6,258,545 B1 | 7/2001 | Meade et al. |
| 6,391,558 B1 | 5/2002 | Henkens et al. |
| 6,740,518 B1 | 5/2004 | Duong et al. |
| 6,753,143 B2 | 6/2004 | Tao et al. |
| 6,761,816 B1 | 7/2004 | Blackburn et al. |
| 6,773,884 B2 | 8/2004 | Mirkin et al. |
| 6,875,619 B2 | 4/2005 | Blackburn |
| 6,960,467 B2 | 11/2005 | Shieh et al. |
| 7,056,669 B2 | 6/2006 | Kayyem et al. |
| 7,393,645 B2 | 7/2008 | Kayyem et al. |
| 7,534,331 B2 | 5/2009 | Kayyem |
| 7,820,391 B2 | 10/2010 | Chunlin |
| 10,001,476 B2 | 6/2018 | Wood et al. |
| 2002/0001844 A1 | 1/2002 | Frutos et al. |
| 2005/0176029 A1 | 8/2005 | Heller et al. |
| 2007/0007148 A1 | 1/2007 | Okada et al. |
| 2008/0073225 A1 | 3/2008 | Paulus |

FOREIGN PATENT DOCUMENTS

| | | |
|---|---|---|
| WO | WO 2008/101196 | 8/2008 |
| WO | WO 2009/061941 | 5/2009 |

OTHER PUBLICATIONS

Anne et al. (JACS 125:1112-3) (Year: 2003).*
Immoos et al., "DNA-PEG-DNA triblock macromolecules for reagentless DNA detection," *Journal of the American Chemical Society* 126(35): 10814-10815 (Sep. 2004).
Mir et al., "Target label-free, reagentless electrochemical DNA biosensor based on sub-optimum displacement," *Talanta* 75(2): 432-441 (Apr. 2008).
Umek et al., "Electronic detection of nucleic acids: a versatile platform for molecular diagnostics," *The Journal of Molecular Diagnostics* 3(2): 74-84 (May 2001).
Xiao et al., "Single-step electronic detection of femtomolar DNA by target-induced strand displacement in an electrode-bound duplex," *Proceedings of the National Academy of Sciences* 103(45): 16677-16680 (Nov. 2006).
Yu et al., "Electronic detection of single-base mismatches in DNA with ferrocene-modified probes," *Journal of the American Chemical Society* 123(45): 11155-11161 (Nov. 2001).

* cited by examiner

*Primary Examiner* — Christopher M Gross
(74) *Attorney, Agent, or Firm* — Roche Molecular Systems, Inc.

(57) ABSTRACT

The invention, depending on aspect and embodiment, relates to capture probe controls, and capture and signal probe configurations and combinations of configurations that can facilitate accurate and efficient multiplex analyte detection, especially in electrochemical detection schemes.

20 Claims, 8 Drawing Sheets

Specification includes a Sequence Listing.

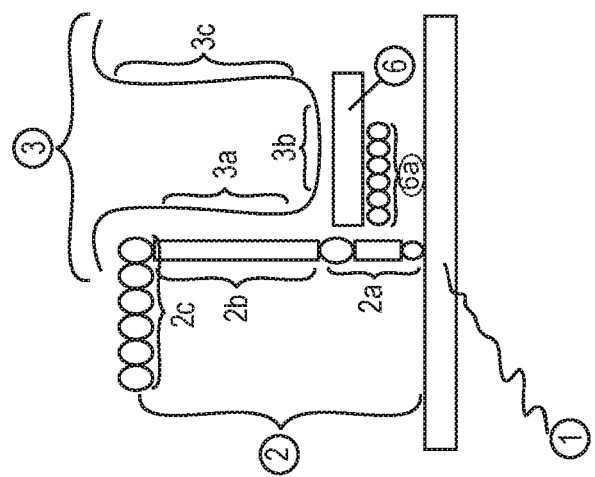
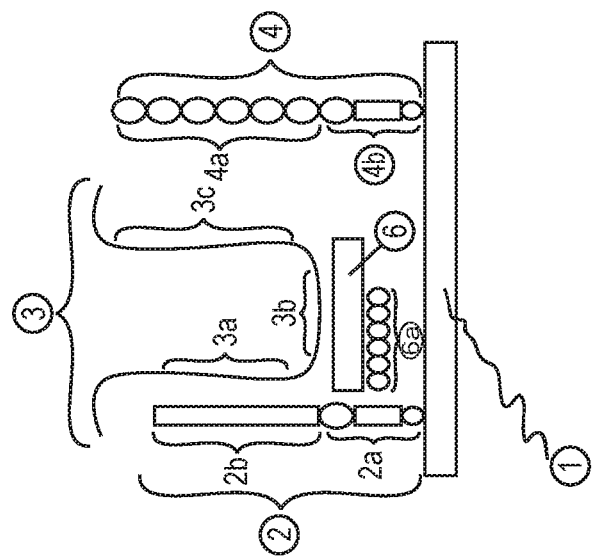
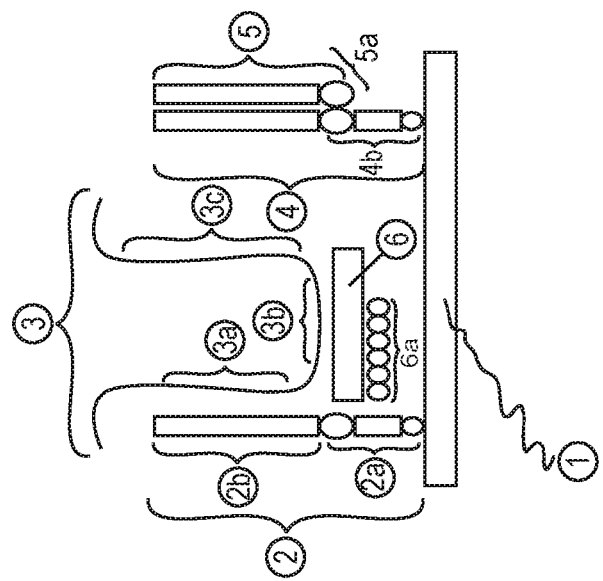

CVEV Amplicon Dilution: 1:1, 1:5, 1:10, 1:20, 1:50

Fig. 4

CVEV Amplicon Dilution: 1:1, 1:5, 1:10, 1:20, 1:50

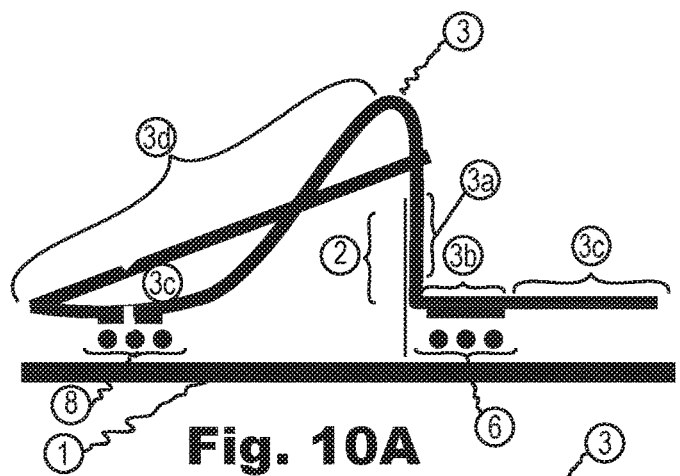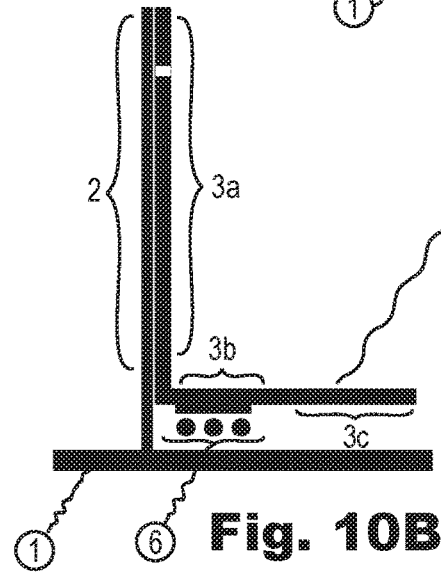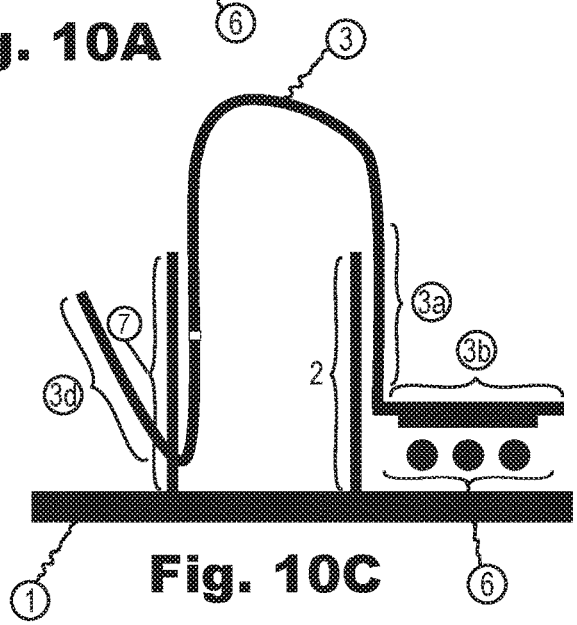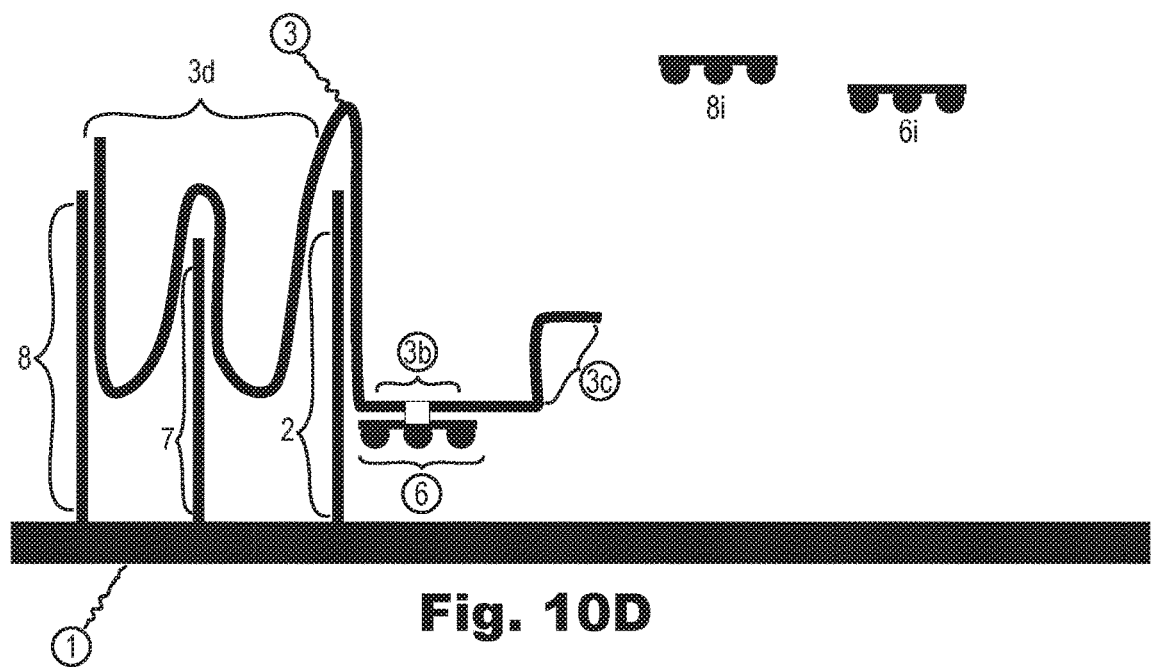
Fig. 10A
Fig. 10B
Fig. 10C
Fig. 10D

CAPTURE LIGAND CONTROLS, BLOCKING PROBES, MASKING PROBES AND METHODS OF USING THE SAME

CROSS REFERENCE TO RELATED APPLICATIONS

This is a continuation of U.S. patent application Ser. No. 15/974,605, filed on May 8, 2018, which is a continuation of U.S. patent application Ser. No. 12/914,257, filed Oct. 28, 2010, issued as U.S. Pat. No. 10,001,476, which claims the benefit of U.S. Provisional Patent Application No. 61/255,713, filed Oct. 28, 2009. The prior applications are incorporated herein by reference in their entirety.

FIELD

The invention, depending on aspect and embodiment, relates to capture probe controls, and capture and signal probe configurations and combinations of configurations that can facilitate accurate and efficient multiplex analyte detection, especially in electrochemical detection schemes.

BACKGROUND

In vitro diagnostic assays are a burgeoning, increasingly sophisticated, field in the health care industry. Many such assays rely on affinity or capture probe deposition to a solid support, followed by incubation with a sample suspected of containing an analyte of interest that specifically binds to the capture probe.

The binding event is then signaled through use of a label of some sort, e.g., colorimetric, radioactive, or electronic. The label can be covalently or noncovalently bound directly or indirectly to a binding pair complement probe, e.g., a capture probe (or, in sandwich assay configurations, a signal probe). In some assays configurations, it can also be attached to analyte before binding to a capture probe, e.g., as in label incorporated into PCR amplified nucleic acid analyte. In electrochemical detection schemes the probe or signal can also be based on the establishment and subsequent perturbation of an electronic property, such as a field or charge potential or current, e.g., as occur in various field effect transistor (FET)-based, surface plasmon-resonance (SPR)-based, and redox-based detection schemes. Electronic-based signaling schemes typically employ electrodes, and these and other signaling schemes are all well-known in the art.

Applicants' commercial eSensor® XT-8 system (GenMark Diagnostics, Inc.; Carlsbad, Calif., USA) is a redox-based electronic detection scheme that makes use of AC/DC voltammetry. Specific technology embodied in Applicants' system is described in detail in exclusively-licensed U.S. Pat. Nos. 6,258,545 and 6,071,699, commonly-owned U.S. Pat. Nos. 7,056,669, 6,740,518, 6,761,816, 7,534,331, 6,960,467, and 6,875,619, and commonly-owned PCTUS08/54136 (published as WO2008101196), the contents of each of which are herein incorporated by reference. Applicants currently offer a variety of multiplex human genotyping assays for use the eSensor® XT-8 system and are working to develop and commercialize multiplex infectious disease testing assays on the same platform.

Infectious disease testing by nature typically generates a much higher percentage of negative results. For a multiplex array-based electronic detection platform such as Applicants' eSensor® XT-8 system, this means that most detection electrodes return no signal in any given infectious disease panel test.

It has not heretofore been possible in Applicants' system to distinguish a non-signaling electrode caused by a true negative sample from a malfunctioning electrode resulting from compromised capture probe integrity or a manufacturing-related problem such as a failure to properly spot capture probe. Moreover, multiplex genotyping systems sometimes feature background signal or noise attributable to adjacent sequence variations that can occur concomitantly with a sequence or residue of interest to be interrogated.

The present invention, depending on aspect and embodiment, addresses either or both of these deficiencies.

SUMMARY

The invention, depending on aspect and embodiment, relates to pad controls, masking signal probes, and blocking capture probes—all of which find particular merit in electronic detection schemes, but which may also benefit other types of detection assay systems.

In a first aspect, the invention features a method of assessing capture binding ligand deposition on the surface of one or more addressable solid support detection sites by attaching one or more capture binding ligands to each site, at least one of which has a measurable label thereon or that can bind another moiety, e.g., a nucleic acid complement, containing such label. The method includes detecting that label as a control measure of the success of capture binding ligand deposition and/or integrity. In preferred embodiments, the labels that are used are electron transfer moieties and the addressable solid support detection sites are detection electrodes spotted with capture probe. In some embodiments, e.g., nucleic acid analyte electrochemical detection embodiments employing detection electrodes, the sites also feature an insulating self-assembled monolayer or mixed monolayer. Some control embodiments can be stand-alone and feature no counterpart binding ligand in an aqueous analyte sample; such controls can be jointly or serially spotted onto the detection site before or after the capture probe that is specific for the analyte of interest is. These controls may or may not contain their own signal that is distinguishable from that which signals analyte binding. If the pad control label is the same as that which signals analyte binding, a measurement is taken before analyte is added, and then after. If the capture binding ligand is properly immobilized, a signal will register, and depending on embodiment, either directly from that capture binding ligand, or else from a surrogate second capture binding ligand. In some second capture binding ligand embodiments, the label may be bonded to the second capture binding ligand complement or binding partner, which will first have to be added to the system, i.e., contacted with the addressable site. In other embodiments, the ligands may have counterpart ligands such that a signal is generated from one or both of the bound and unbound capture ligands, and another distinct signal is generated upon counterpart binding. One advantage of redox-mediated electronic detection is that there is a variety of different electronic transfer moiety labels each having its own distinct potential that can be selectively measured or filtered.

In a second aspect, the invention features a method of discriminating against a known interfering nucleic acid residue that may be present in a nucleic acid sequence of interest, e.g., in an analyte sample. The nucleic acid sequence has a residue of interest to be tested for and the method includes providing first and second nucleic acid probes each having a label, with the first labeled probe complementary to the sequence of interest that includes the interfering nucleic acid residue and the second labeled probe complementary to the sequence of interest that does not include an interfering nucleic acid residue. The method then includes adding a test nucleic acid sample and testing it for the nucleic acid residue of interest, preferably under stringent discriminating conditions. In preferred embodiments the labels are identical, but they need not be. Preferably they are energy transfer moieties, most preferably ferrocene-based or ferrocene-derivative compounds. The method might be, e.g., a genotyping, isotyping or expression assay.

In a third aspect, the invention features a method of reducing background signal or enhancing signal to noise ratio in a multiplex electrochemical detection assay system employing energy transfer moiety-labeled nucleic acid signal probes, at least two detection electrodes, and that tests for multiple nucleic acid residues of interest on a common nucleic acid sequence of interest. The method includes providing first and second detection electrodes each having one or more nucleic acid capture probes attached. The capture probes are specific for a nucleic acid sequence of interest that comprises two separated nucleic acid residues of interest, one of whose presence is to be tested for on one detection electrode and the other of whose presence is to be tested for on another electrode. The object is to minimize or suppress both sequences being detected on the same detection electrode. The labeled nucleic acid signal probes can be of the same or different redox potentials and each probe is specific for a different portion of the common nucleic acid sequence of interest, each including a different nucleic acid residue of interest to be analyzed. The method includes forming hybridization complexes on the first and second detection electrodes under conditions wherein the signal probe specific for the nucleic acid residue to be tested for on the first detection electrode is held in closer proximity to the first detection electrode relative to the second detection electrode, and wherein that relationship is reversed for the second electrode. The method includes testing for the presence of those hybridization complexes on the respective electrodes under conditions wherein the signal probe closest to the electrode transfers electrons thereto with greater frequency or occurrence than the signal probe that is further away. To accomplish this, the method can make use of one or more capture probes on the same detection electrode. When multiple capture probes are used, each is specific for a different portion of the common nucleic acid sequence of interest. The nucleic acid sequence of interest can be unamplified nucleic acid or else amplified nucleic acid, e.g., through PCR. In some embodiments, the electrodes preferably have a self-assembling monolayer ("SAM"), more preferably a mixed SAM of two or more species, each species featuring different chain lengths, conjugated bond numbers (if any) and/or substituents (if any).

In a fourth aspect, the invention features compositions and kits for performing one or more of the above aspects and embodiments.

As the person of skill in the art will appreciate, any of the above aspects, embodiments, and variations thereon, including those recited in the claims to follow, may be combined as appropriate within the spirit of the invention.

BRIEF DESCRIPTION OF THE DRAWINGS

FIGS. 1A-1C illustrate three different pad control embodiments.

FIG. 4 shows diluted CVEV amplicon signals at two electrode control deposition concentrations.

FIG. 5 shows QW80 electrode control signals at different CVEV amplicon concentrations.

FIGS. 6A-6B shows N6 and QW80 signals generated from CVEV target mimics (N6) (FIG. 6A) and different electrode controls (QW80) (FIG. 6B).

FIGS. 7A-7B shows N6 and QW80 signals generated from different dilutions of CVEV amplicon (N6 signal) (FIG. 7A) and electrode control MW1106 (QW80 signal) (FIG. 7B).

FIGS. 10A-10D show the problem of spillover (A), followed by various possible solutions (B)-(C).

SEQUENCE LISTING

Figures 2, 3:
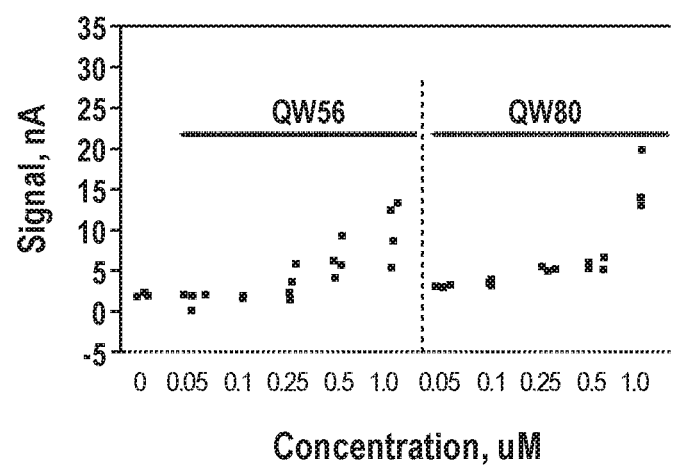
FIG. 2 shows QW56 and QW80 electrode control signals at a range of concentrations.
FIG. 3 shows CVEV amplicon signals at different electrode control concentrations.

The Sequence Listing is submitted as an ASCII text file 9823-100157-04_Sequence_Listing.txt, Apr. 27, 2020, 4 KB, which is incorporated herein by reference.

DETAILED DESCRIPTION

Definitions

As used in the claims and herein, the following terms have the following definitions:

A "solid support" may be anything other than an aqueous phase at room temperature and include, e.g., beads, gels, columns, column matrices, multi-titer plates, paper, membranes, printed circuit boards, or other array surfaces or supports;

The term "immobilize" or derivative term thereof, includes affixation, association or binding, whether covalently or noncovalently.

A "capture binding ligand" is synonymous with a "capture probe" or "capture binding probe" and is a compound that exhibits a relatively strong or specific affinity for another compound such that it is capable of abstracting that compound away from a group of other compounds in a mixture of compounds. The capture binding ligand may be a protein, carbohydrate, nucleic acid, small molecule, or any combination of these.

An "analyte" is anything that can selectively bind a capture binding ligand, and may include any of the same items or combination of items that a capture binding ligand can include, although each need not be the same or consist of the same for any given binding pair combination. Analytes may be natural, biological or synthetic, e.g., as in any of synthetic or other molecules used for drug discovery that manifest unusually good or specific binding affinity to a "capture binding ligand." Both analytes and capture binding ligands may consist of one or more different domains. Where these are nucleic acids, unless otherwise specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain. The person of skill will appreciate that complementary orientations between the analyte and capture binding ligands are necessary.

By "analyzing" is meant measuring, detecting or determining the presence, absence or composition of something.

By "label" is meant something that can signal or be stimulated to signal an event or the presence of a molecule or complex of molecules. Labels may include, e.g., dyes, radioactive atoms or molecules, redox-active compounds, enzymes, enzyme substrates, nucleic acids, derivatives thereof the like. Redox-active labels come in a variety of different potentials that can be used, similar to the existence of different color dyes and chemiluminscent compounds.

By "signal probe" is meant a probe molecule that bears a label of some sort that can bind to and signal the presence of analyte. Preferred embodiments are ferrocene and ferrocene-derivative bearing nucleic acids, which bind to one domain of analyte while another domain of the analyte binds to the capture binding ligand on a solid support surface site (configurations known colloquially as "sandwich assays").

By "redox-active" compound or moiety is meant one capable of transferring, shuttling or receiving electrons from another redox-active compound. Preferred redox-active compounds include electrodes and metallocenes, for the latter preferably ferrocenes and derivatives thereof.

By "array" is meant a plurality of distinct sites bearing different capture binding ligands. The array is preferably "addressable" insofar as the individual sites have a predetermined or determinable location relative to one another, optionally with the help of electronic connectors and/or software.

By "blocking probe" is meant a nucleic acid sequence that prevents a certain type of background electronic signal from being generated by fixing its complement signal probe at a non-signaling distance from a detection electrode. See, e.g., FIG. 10. The figure shows insoluble forms/schemes of blocking "capture" probes. As the person of skill will also appreciate, [a] soluble blocking probe(s) can also be used if it/they bind(s) more tightly or with greater frequency relative to the undesired signal probe(s) that is not intended to be measured (produce "signal spillover" on a given electrode). For example, peptide nucleic acids are known to bind more tightly, and/or one could use longer natural "blocker" sequences that overall have a higher melting temperature (TM) than the undesired signal probe and/or one could supply more of the "cold" blocker(s) relative to the undesired signal probe(s) that would otherwise create "spillover" (outcompete them kinetically and/or thermodynamically).

By "masking probe" is meant a signal probe nucleic acid species that has affinity not just for the interrogation sequence of interest, but also for a neighboring sequence variation as well, such as to allow overall signaling in the presence or absence of the neighboring sequence variation. See, e.g., FIG. 9.

By "infectious disease" is meant one bottomed in the presence of an infectious disease marker, agent or target, whether it be viral, bacterial or fungal. Illustrative infectious diseases targets include, e.g., natural, synthetic or amplified biomolecules such as: (1) viruses, including but not limited to, orthomyxoviruses, (e.g. influenza virus), paramyxoviruses (e.g. respiratory syncytial virus, mumps virus, measles virus), adenoviruses, rhinoviruses, metapneumoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-1 and -11), papovaviruses (e.g. papillomavirus), polyomaviruses, and picornaviruses, and the like; and (2) bacteria, including but not limited to, a wide variety of pathogenic and non-pathogenic prokaryotes of interest including *Bacillus; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botuliniin, C. tetani, C. difficile, C. perfringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *G. lamblia Y. pestis, Pseudomonas*, e.g. *P. aeruginosa, P. putida; Chlamydia*, e.g. *C. trachonmatis; Bordetella*, e.g. *B. pertussis; Treponema*, e.g. T. palladium; and the like. In preferred embodiments the targets are human-specific infectious disease agents or targets, with the markers or targets preferably being nucleic acid markers.

By "electrode" is meant a composition, which, when connected to an electronic device, is able to sense a current or charge and convert it to a signal. Thus, an electrode is an ETM as described herein. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide (Mo206), tungsten oxide (W03) and ruthenium oxides; and carbon (including glassy carbon electrodes, graphite and carbon paste). Preferred electrodes include gold, silicon, carbon and metal oxide electrodes, with gold being particularly preferred.

By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. The SAM may comprise conductive oligomers alone, or a mixture of conductive oligomers and insulators. As outlined herein, the use of a monolayer reduces the amount of non-specific binding of biomolecules to the surface, and, in the case of nucleic acids, increases the efficiency of oligonucleotide hybridization as a result of the distance of the oligonucleotide from the electrode. Thus, a monolayer facilitates the maintenance of the target analyte away from the electrode surface. In addition, a monolayer serves to keep charge carriers away from the surface of the electrode. Thus, this layer helps to prevent electrical contact between the electrodes and the electronic transfer moieties (ETMs; redox-active), or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer can thus serve as a physical barrier to block solvent and undesired signal ("noise") accessibility to the electrode.

I. Pad Controls

These are expected to find the greatest utility in electrochemical detection applications but can apply to other detection schemes as well. The general principle is illustrated in FIG. 1: Pad Controls verify capture probe (2) deposition and/or integrity on the electrode surface (1) by using a redox moiety (4a, 5a and/or 2c) fastened directly or indirectly via hybridization to the capture probe or a second surrogate "dummy" capture probe (4). The success of deposition is gauged by the presence or absence of that signal. This is important because previously it has not been possible to distinguish a non-signaling electrode that is caused by a true negative sample from a malfunctioning electrode that results e.g., from a manufacturing-related problem such as failure to effectively spot the capture probe on the electrode.

To solve this problem the redox moiety or moieties (4a, 5a and/or 2c) are attached as for signal probes (6), which labels can be introduced at either terminus or anywhere in the middle of the sequence, and then spotted onto the electrode (1) surface by conventional means as described above. In dummy capture probe strategies (FIG. 1A), one can also leave the signal off the dummy capture probe itself and instead use a signal probe (5) that is specific for the dummy capture probe, and that contains its own label (5a). Regardless of the specific pad control scheme chosen (FIG. 1A, 1B or 1C), the control label (4a, 5a and/or 2c) is preferably of a different potential than the corresponding signal probe (6) signal (6a) to be detected on that electrode surface and, in the instance of the label being a part of a signal probe (5) specific for a dummy capture probe (4), the sequence of the capture probe should preferably not cross-hybridize with any other sequences on the platform save the signal probe that is specific for the dummy capture probe. Example 1 speaks further to the concept and its applications.

In each of FIGS. 1A-C, the target (3), which could be synonymous with a PCR amplicon sequence in nucleic acid embodiments, has a portion (3b) which binds or hybridizes specifically to a desired signal probe (6), a portion (3a) which binds or hybridizes to a corresponding capture probe portion (2b) and optionally one or more portions flanking that, e.g., (3c; see also 3d in FIG. 10). Linkers (2a) preferably link, join or bond the capture probe (2) to the electrode surface (1). As pictured, the labeled portions or labels (6a, 5a, 4a, 2c) look to be separate entities, but in reality can be conjugated or internal to the probe itself (6, 5, 4, 2) e.g., as a feature of the probe's synthesis or post-synthesis, e.g., in the instance of DNA probe synthesis/label attachment. Not pictured is a self-assembled monolayer (SAM), which is also attached to the electrode surface in preferred embodiments via one or more linkers in similar format to the capture probe linkers (2a), and which serves to prevent or lessen undesired electron transfer events ("noise") to the electrode surface.

II. Masking Probes

Figure 9:
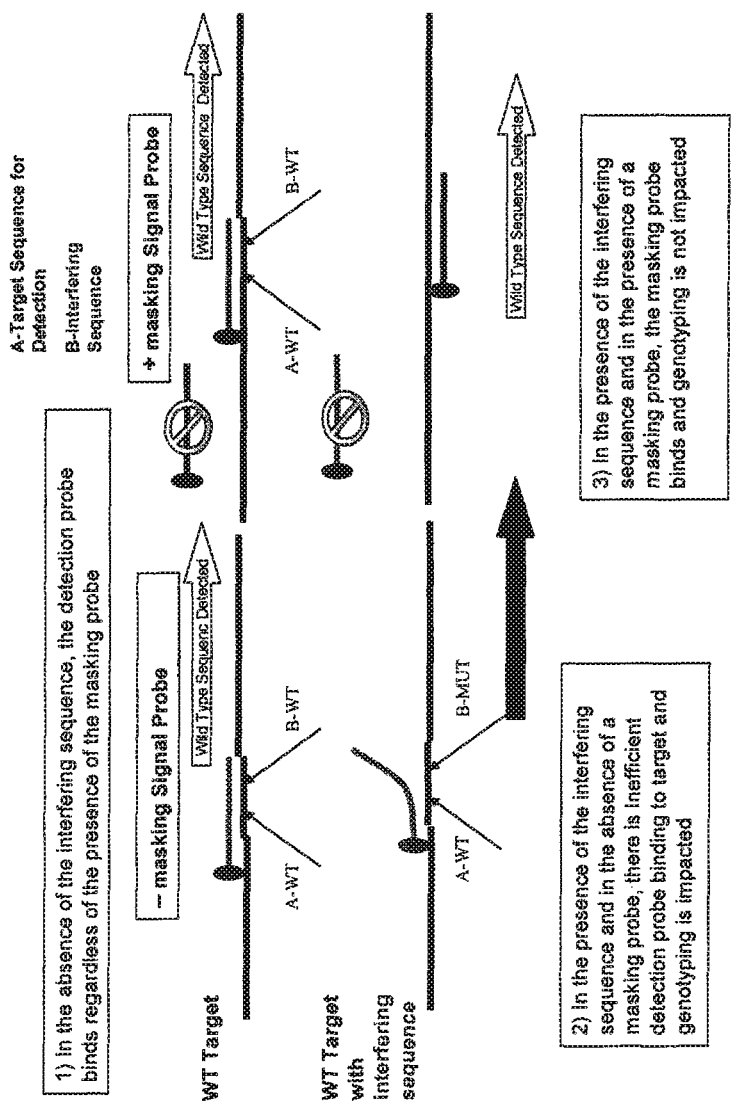
FIG. 9 shows a masking probe scheme and why it is needed.

The masking probe concept is illustrated with respect to FIG. 9 and nucleic acid detection embodiments. Briefly, to guard against the situation where there is a possible neighboring mutation to the one of interest to be detected, and were such neighboring sequence indeed to be present, it might interfere with binding and hence proper signaling. To address this, one supplies two labeled probes, one with and one without the undesirable neighboring mutation or sequence deviation, such that one of the signal probes is assured to bind the target sequence appropriately and signal the presence of the residue or series of residues desired to be detected.

III. Blocking Probes

The blocking probe concept is illustrated with respect to FIG. 10 and "multiplex" electrochemical detection schemes on electrode surfaces, where different binding events and signals are intended to be detected on different, but not the same, electrode surfaces. The problem is illustrated with respect to FIG. 10A. The target (3) contains multiple interrogation sites (3b, 3c) that are separated from one another, each to be tested and determined on a different electrode surface. Because electrode signal is a function of proximity to electrode surface, with close proximation to electrode resulting in signal, the undesired second interrogation site (3c) should somehow be "blocked" (i.e., kept further away from the electrode or else otherwise prevented from binding a second signal probe (8) specific for the sequence or portion (3c) that is not to be detected on that particular electrode surface. This can be accomplished using a variety of different schemes, e.g., as reflected in FIGS. 10B-10D. In FIG. 10B for example, the capture probe (2) is of lengthened design to pin the interfering site away from the electrode surface. In FIGS. 10C and 10D, additional capture probes (7, 9) are introduced to accomplish similar effect. Soluble signal probes (before they bind) are denoted by 6i and 8i, with 6i being the intended signal probe and 8i being the unintended signal probe that is desired "blocked". This particular figure does not show linkers as per FIG. 1, but those too are preferably present.

Other detection electrodes in a multiplex detection system are configured reciprocally to ensure that they only register their particular site or sites to be interrogated, and not the unwanted other(s). For example, with respect to FIG. 10, on a different detection electrode signal probe 8i may be desired to be measured instead of 6i, and its electrode and capture probe are configured accordingly, etc., etc.

IV. Probe Synthesis, Functionalization and Conjugation—Generally

Probe synthesis, functionalization and conjugation are all well-known techniques in the art, e.g., as described in the patents and publications cited herein, and in the following handbook references: Kissinger and Heineman, Eds., Laboratory Techniques in Electroanalytical Chemistry; 2d Ed., MARCEL DEKKER, INC., NY, NY, USA (1996); Biochip Technology, Cheng and Kricka, Eds. George H. Buchanan Printing Company, Bridgeport, N.J. (2001); Bard and Faulkner, Eds., Electrochemical Methods: Fundamentals and Applications, 2d Ed., John Wiley & Sons, Inc., Hoboken, N.J., USA (2001); Microarrays: Preparation, Microfluidics, Detection Methods, and Biological Applications, K. Dill et al., Eds., Springer Science+Business Media, LLC, NY, NY, USA (2009); Integrated Biochips for DNA Analysis, Biotechnology Intelligence Unit, Liu and Lee, Eds., Landis Bioscience, Springer Science+Business Media, LLC, NY, NY, USA (2007). Each of the foregoing and the references cited therein are herein incorporated by reference for convenience and are illustrated herein with respect to nucleic acids as binding ligands and probes. As the personal of skill will appreciate, there is a whole body of readily accessible and implementable information for other types of binding ligands and probes as well.

Nucleic acid signal and capture probes are typically designed to be complementary to a roughly 40- to 50-base sequence within the target. The capture probe sequence is usually complementary to the 3'-region of the target (but the reverse—5'—can also be true), and is designed to have a melting temperature (TM) of ~50° C. Capture probes can be modified either at the 3'end or the 5' end with a disulfide linker for covalent attachment to a gold electrode surface, e.g., as essentially described in commonly owned U.S. Pat. Nos. 6,753,143 and 7,820,391, each of which is herein incorporated by reference. The signal probe sequence(s) is/are complementary to (a) specific region(s) of the target, and is/are designed to have minimum TM(s) of about 5 to 10° C. below that of the capture probe. If sequence discrimination is needed, the sequence polymorphism should be as close as possible to the center of the signal probe sequences, and the TM's of the two signal probes should be as closely matched as possible. The sequence gap between the signal and capture probes should be zero to two bases. Ferrocene labels (typically 6 labels per probe) are added to the 5'-terminus of the signal probe sequence(s). Since all hybridization reactions must take place at a single temperature, the TM values of all signal probes should be within a range of 5° C. Since all detection reactions must occur within the same solution, signal and capture probes must be designed to avoid any cross-hybridization; particularly between signal probes and capture probes; maximum $\Delta G_0$ values for cross-hybridization have been empirically established.

Capture probes, including, e.g. nucleic acids, can be adhered to electrodes or other substrate surfaces directly or indirectly, covalently or noncovalently, using a variety of well-known techniques. See, e.g., Ch. 13, Chemically Modified Electrodes, Martin and Foss, pp. 403-442, Laboratory Techniques in Electroanalytical Chemistry; 2d Ed., Kissinger and Heineman, Eds., MARCEL DEKKER, INC. (1996); Biochip Technology, Cheng and Kricka, Eds. George H. Buchanan Printing Company, Bridgeport, N.J. (2001). In preferred embodiments, this is done by mixing disulfide self-assembling monolayer insulator precursors along with a disulfide group-bearing 3' or 5' modified nucleic acid capture probe as described above and spotting onto gold or gold-plated electrodes. This is preferably mediated by a linker/functional group, e.g., W330, as referenced and described in commonly owned U.S. Pat. No. 7,820,391, or N150 as referenced and described in commonly owned U.S. Pat. No. 6,753,143. As the person of skill will appreciate, there are many types of linkers available, e.g., as described in the preceding referenced documents.

Linker N152 is utilized in the Examples that follow. It is a "forward" linker such that the disulfide attachment group resides at the 3' end of the resultant capture probe. It is essentially N150 as described in commonly owned U.S. Pat. No. 6,753,143, but functionalized as follows to enable controlled porous glass (CPG) addition as a precursor to routine solid phase oligonucleotide synthesis:

Synthesis of N152.

To a solution of N150 (0.3 g, 0.45 mmol) in pyridine (20 mL) was added DMAP (20 mg) and succinic anhydride (0.9 g, 9.01 mmol). The reaction mixture was stirred at room temperature overnight. The mixture was diluted with dichloromethane, washed by 10% copper sulfate, dried over sodium sulfate and concentrated. The residue was purified on a column of 50 g silica gel. The column was packed in 1% TEA in hexane and eluted with 1% TEA and 3% methanol in dichloromethane to give the desire product N152 (0.3 g, 90%). $_1$H NMR (300 MHz, CDCL3) δ 7.23-7.49 (m, 9H), 6.86 (d, J=8.7 Hz, 4H), 4.22 (t, J=6.3 Hz, 2H), 3.82 (s, 6H), 3.03-3.17 (m, 4H), 2.66-2.78 (m, 6H), 2.07 (m, 2H), 1.60-1.74 (m, 4H), 1.29 (m, 27H); Anal. calcd. for ($C_{44}H_{62}O_7S_2$) 766, found 766.

Synthesis of N152-CPG-1400.

A heterogeneous mixture of CPG (2.0 g, pore size 1400A), N142 (0.1 g, 1.0 eq.), hydroxybenzotriazole (20 mg, 1.1 eq.), BOP (66 mg, 1.1 eq.) and TEA (0.5 mL) in dichloromethane was shaken on a shaker overnight. The CPG was filtered and washed by dichloromethane (2×30 mL), and was transferred to another flask. To the flask containing CPG were added pyridine (8 mL), acetic anhydride (2 mL) and N-methylimidazole (0.4 mL). The mixture was shaken on a shaker for 2 hours. The CPG was filtered, and washed by pyridine (2×30 mL), methanol (2×30 mL), dichloromethane (2×30 mL) and ethyl ether (2×30 mL). The CPG was dried on a vacuum line for 2 hours. The loading of desired N152-CPG was 30 mol/g.

EXAMPLES

Example 1: Pad Controls

The goal of this electrochemical detection embodiment study was to show feasibility using a ferrocene-labeled control molecule to generate signal in the presence or absence of the amplified assay target to verify function of all target electrodes. The control is not wed to ferrocenes or ferrocene derivatives as labels; any redox active moiety(ies) can be used. Three possible methods for an electrode control are shown in FIG. 1.

In method 1, the control molecule is a separate and distinct unlabeled capture probe sequence that is non-homologous to any target sequence (analyte of interest) and specifically binds a labeled complement upon introduction of that complement as part of the signal buffer. This complement binds at every detection electrode containing the control capture probe and is detected at the completion of hybridization, irrespective of the presence of assay (analyte) target. The control label is selected so that it generates an electrochemical potential that can be distinguished from the label used to detect the presence of target analyte—typically a PCR amplified product from a biological sample.

Method 2, by contrast, utilizes a directly-labeled capture probe and avoids the requirement of the direct target used in Method 1. This method, however, requires that the label be introduced to the capture probe spotting equipment—a potential source of contamination in the manufacturing line that may lead to non-specific background signals across different product lines if the same spotting equipment is use).

Method 3 similarly requires that each target capture probe be directly labeled (not via a complement added later) and therefore suffers the same drawback if the same spotting equipment is to be used. Again, the label should be different from the one used in the signal probes to detect the (amplified) target analyte of interest.

To examine the feasibility of the foregoing pad control possibilities, method 2 was selected in the following study. Two control molecules that incorporated 6× QW56 or 6× QW80 ferrocene labels were prepared using routine DNA synthesis techniques essentially as described in commonly owned application PCT/US08/82666 (published as WO/2009/061941A2 and U.S. Pat. No. 7,820,391). N6 is another label that can be used; its synthesis is described in commonly owned U.S. Pat. No. 7,393,645.

MW1105: (QW56)-T-(QW56)-T-(QW56)-T-(QW56)-T-(QW56)-T-(QW56)-N152 (SEQ ID. NO: 1)

MW1106: (QW80)-T-(QW80)-T-(QW80)-T-(QW80)-T-(QW80)-T-(QW80)-N152 (SEQ ID NO: 2)

A range of deposition solutions was then prepared each containing a different concentration of one of the control molecules; 0, 0.05, 0.1, 0.25, 0.5, or 1.0 µM, in the absence or presence of 8 µM capture probe for enterovirus (CVEV), MW1341:

MW1341:
(SEQ ID NO: 3)
GTC-GGT-TCC-GCT-GCA-G-N152

These solutions were then used to spot XT-8 cartridge gold electrode surfaces with the layout set forth in Table 1:

TABLE 1

Electrode Control Pad Layout

| Capture Probe Control | Electrode | Capture Probe | Electrode |
|---|---|---|---|
| Negative Control | 5, 6 | CVEV (8 μM) | 41, 42 |
| Positive Control | 8, 9 | CVEV (8 μM) + MW1105 (0.05 μM) | 44, 45 |
| MW1105 (0.05 μM) | 11, 12 | CVEV (8 μM) + MW1105 (0.1 μM) | 47, 48 |
| MW1105 (0.1 μM) | 14, 15 | CVEV (8 μM) + MW1105 (0.25 μM) | 50, 51 |
| MW1105 (0.25 μM) | 17, 18 | CVEV (8 μM) + MW1105 (0.5 μM) | 53, 54 |
| MW1105 (0.5 μM) | 20, 21 | CVEV (8 μM) + MW1105 (1 μM) | 56, 57 |
| MW1105 (1 μM) | 23, 24 | CVEV (8 μM) + MW1106 (0.05 μM) | 59, 60 |
| MW1106 (0.05 μM) | 26, 27 | CVEV (8 μM) + MW1106 (0.1 μM) | 62, 63 |
| MW1106 (0.1 μM) | 29, 30 | CVEV (8 μM) + MW1106 (0.25 μM) | 65, 66 |
| MW1106 (0.25 μM) | 32, 33 | CVEV (8 μM) + MW1106 (0.5 μM) | 68, 69 |
| MW1106 (0.5 μM) | 35, 36 | CVEV (8 μM) + MW1106 (1 μM) | 71, 72 |
| MW1106 (1 μM) | 38, 39 | | |

Relative signal intensities for each of the above combinations were then determined through the covalently attached QW56/QW80 labels. The results in FIG. 2 show the signals obtained in the presence of 8 μM CVEV capture probe but in the absence of CVEV amplicon. A deposition solution concentration of >0.25 μM of either control was required to reproducibly detect signal (~5 nA) above background. At the highest concentration, 1 μM, signals had increased to up to ~15-20 nA with the QW80 molecule.

A second experiment was done to investigate whether the presence of the electrode control molecule affected the efficiency of hybridization and signaling of CVEV amplicon (below). The results in FIG. 3 show no drop off in CVEV signal (N6-ferrocene labeled signal probe) across the entire electrode control concentration range.

Next, an experiment was done to assess the effect of changes in CVEV amplicon and electrode control concentration on signal. Serial dilutions of CVEV amplicon were prepared from 1:1 to 1:50 and analyzed on the XT-8. N6 signal was determined at electrodes modified with CVEV capture probe only or with CVEV capture probe co-spotted with 0.5 or 1 μM MW1106 (QW80) electrode control. The results showed the expected amplicon concentration-dependent change in CVEV signal but there was no difference between CVEV signals obtained at electrodes that were modified with CVEV capture probe+electrode control or were modified with CVEV capture probe only (FIG. 4). These electrodes were also analyzed for the QW80 signal generated by the control and no clear changes were observed between the highest and lowest CVEV amplicon concentration (FIG. 5).

These experiments showed that the electrode controls molecules can be co-spotted successfully at a range of concentrations (up to 1.0 μM) with target capture probe and generate a distinguishable signal without compromising the ability of the target capture probe to hybridize and generate detectable signal from an amplified RNA target.

In order to investigate the other electrode control strategies outlined in FIG. 1 cartridges were prepared that contained electrode control designs corresponding to Methods 1 and 2. Methods 1 (MW1449) and 2 (MW1106) control designs were co-spotted with a different CVEV capture probe MW1428 at a higher concentration than earlier studies (4 μM) in order to obtain clear and reproducible signals from the controls. The CVEV capture probe concentration was varied between 8 and 12 μM to investigate whether the higher concentration of capture probe enhanced the sensitivity of the assay. The method 1 capture probe, MW1449, was designed to have no homology with any assay targets. A complementary QW80-labeled direct target for this sequence, MW1450, was synthesized and added to the signal buffer at a concentration of 10 nM:

```
MW1106:
                                  (SEQ ID NO: 2)
(QW80)-T-(QW80)-T-(QW80)-T-(QW80)-T-(QW80)-
T-(QW80)-N152

MW1449:
                                  (SEQ ID NO: 4)
CAC-TTT-GCA-CCG-TCA-GGT-CCA-GTG-N152

MW1450:
                                  (SEQ ID NO: 5)
(QW80)-T-(QW80)-T-(QW80)-T-(QW80)-T-(QW80)-
CAC-TGG-ACC-TGA-CGG-TGC-AAA-GTG

MW1428:
                                  (SEQ ID NO: 6)
CCA-AAG-TAG-TCG-GTT-CCG-C-N152
```

Figures 6A, 6B:
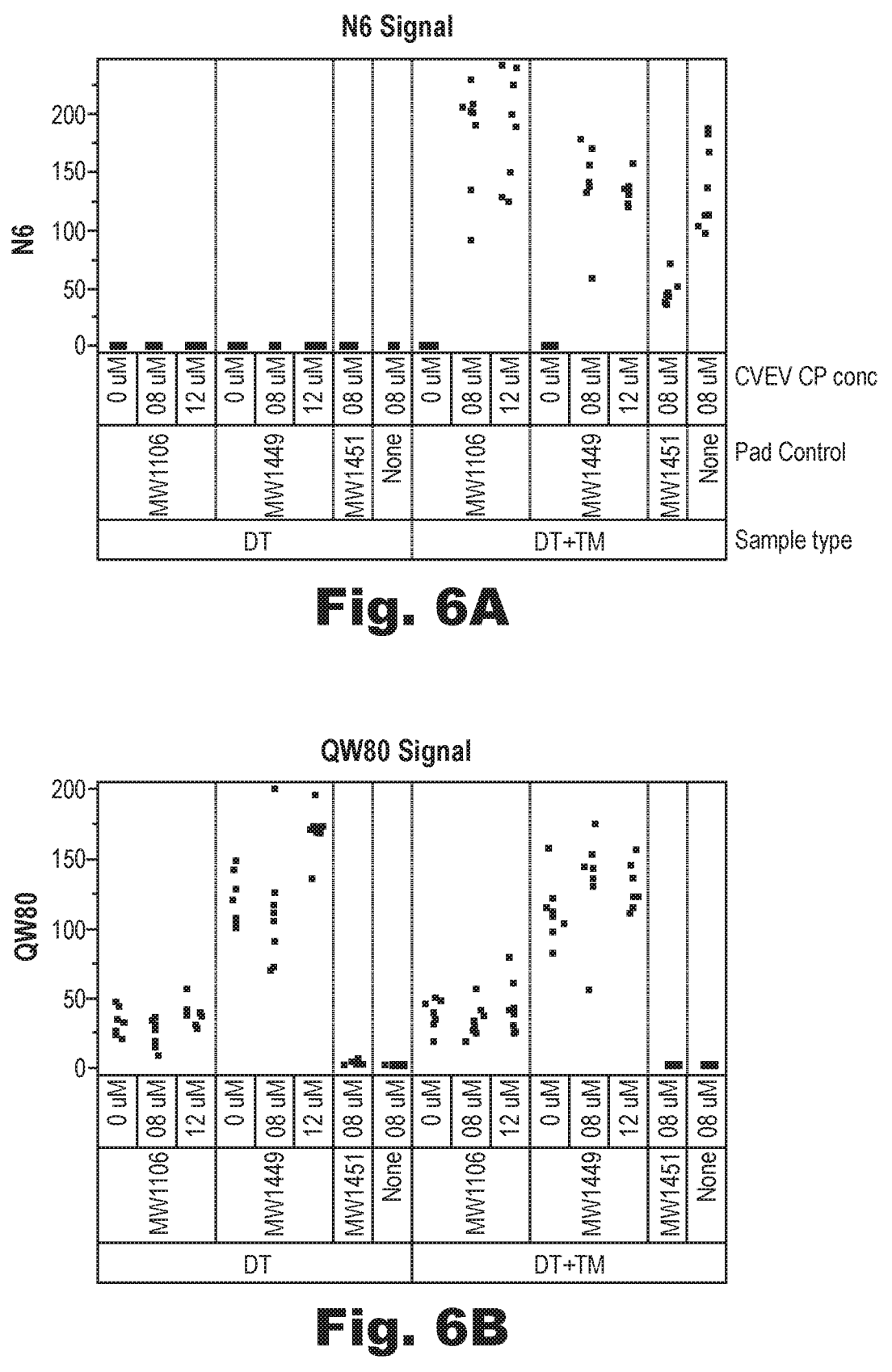

N6 and QW80 signals obtained in the presence and absence of CVEV target mimic are shown in FIG. 6. N6 CVEV signal was clearly observed in the presence of MW1449 and MW1106 although signal with MW1106 appeared slightly higher.

QW80 signals obtained from MW1106 ranged between ~10-50 nAmps and were not affected by the presence of the target mimic. Similarly, QW80 signals generated by MW1449/M1450 hybrid pair were similar in the presence or absence of the target mimic but overall signals were higher than with MW1106 (~75-200 nAmps).

Overall, this experiment showed that both electrode control methods 1 and 2 generated sufficient signal for their intended purpose without compromising target mimic-mediated N6 CVEV signal probe signal.

Figures 7A, 7B:
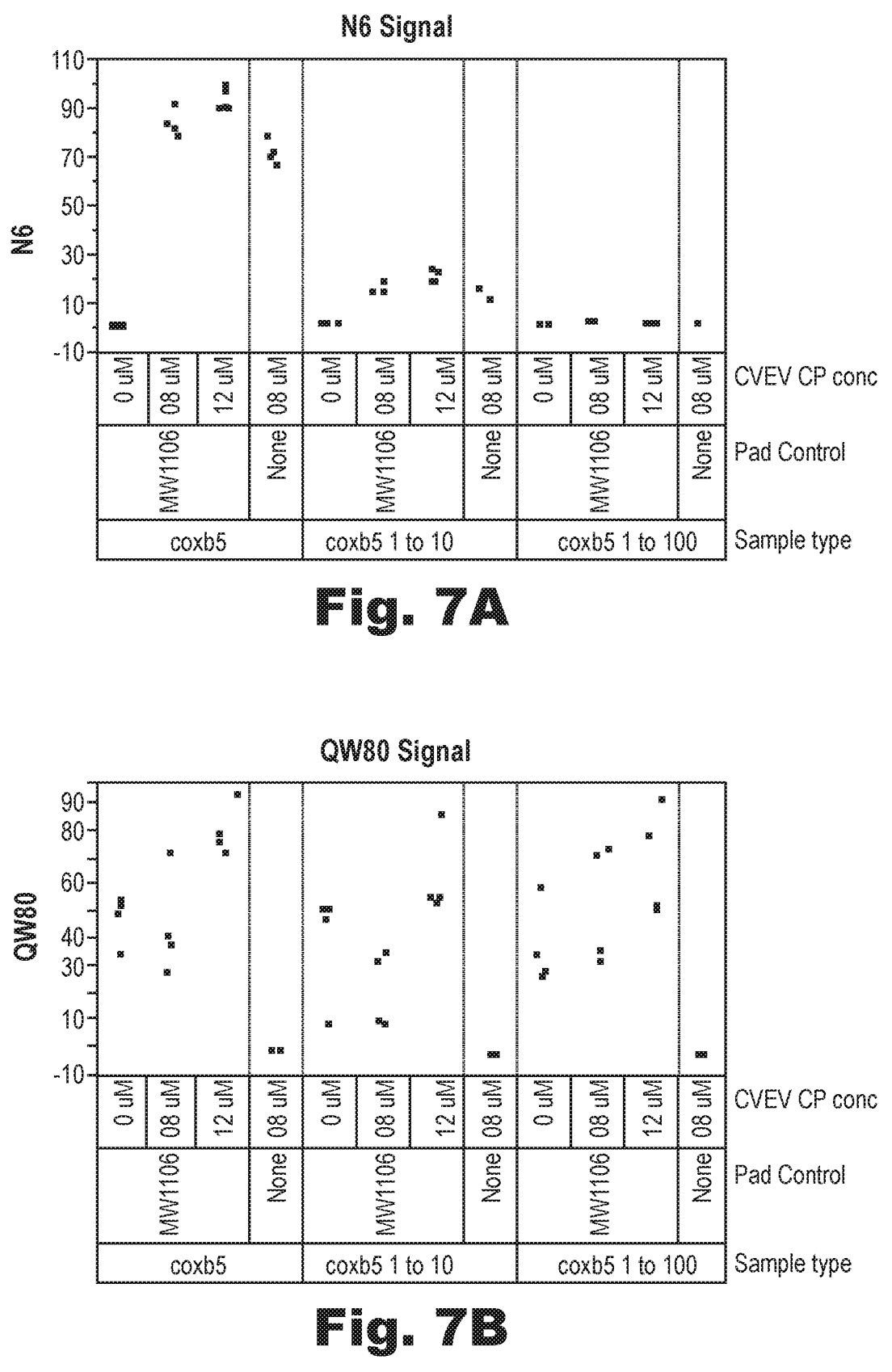

A follow-up experiment was done to analyze different dilutions of CVEV amplicon (coxsackie B5: 1:1, 1:10, 1:100) and electrode control signals in the presence or absence of CVEV capture probe (8 μM or 12 μM depo. concentration) and electrode control molecule MW1106. The results (FIG. 7) showed that CVEV N6 signal was not altered in the presence of the electrode control at 1:1 or 1:10 dilutions (the 1:100 dilution generated very low signal under any condition). N6 signals were slightly higher at the electrodes corresponding to 12 μM CVEV capture probe deposition solutions.

QW80 (electrode control) signals were clearly detected across the different cartridges and electrodes (range ~10-90 nAmps) and were not impacted by the presence of CVEV amplicon.

In a next round of experiments cartridges were spotted with capture probes for 18 respiratory viruses and 4 controls. All capture probes were spotted at 12 μM concentration in the presence of 4 μM electrode control MW1106 (Method 2, FIG. 1).

Figure 8:
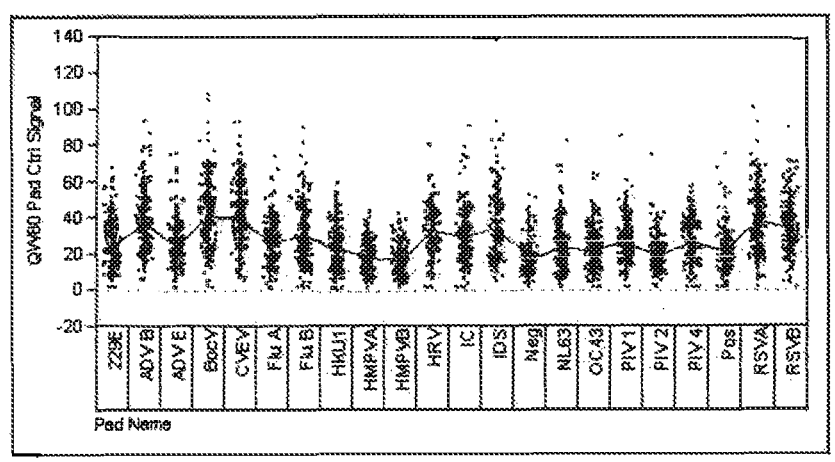
FIG. 8 shows QW80 signals generated from electrode control MW1106 at different respiratory virus/control capture probe electrodes.

The electrode control signal (QW80) generated from multiple cartridges was analyzed (5000 data points) and the distribution of signal across all target electrodes is shown in FIG. 8.

The average QW80 signal was 27.2 nAmps (SD=15.2). The voltammograms produced from the 62 lowest signaling electrodes (0-1 nAmps) were visually analyzed to determine the cause of the low signals and this indicated that all electrodes were not functional due to e.g. electrical connection failure at the electrode. However, of the 62 failed electrodes, only 11 generated a reported error message that would remove it from the data analysis process. Thus the low signals from the remaining 51 electrodes would be included in the data analysis process and potentially generate false results in the assay. However, when a minimum acceptable cut-off signal for the electrode control was applied to the assay (1 nAmp in this example) all 62 failed electrodes were detected and removed from the data analysis process. Thus the chance of producing false results from these non-functioning electrodes was eliminated due to the inclusion of an electrode control in the assay.

Example 2: Masking Signal Probes

The masking signal probe concept is demonstrated with reference to FIG. 9. This can be, though need not be, combined with the other invention aspects. As discussed above, masking signal probes mask the affect of an interfering mutation on the detection of one or more nearby mutations or deletions of interest on the same target nucleic acid or amplicon in genotyping or target detection diagnostics. The solution is to provide, in addition to a signal probe that does not contain a sequence variation at the interfering mutation site, a second signal probe, i.e., "masking probe," that does contain a sequence variation complementary to the interfering mutation as well as the desired interrogation sequence or sequences.

The masking probe is labeled with the same label as the main signal probe so that the interrogation sequence is detected whether the interfering mutation is present or not. The masking probe does not bind with high affinity in the absence of the interfering sequences, so it does not interfere with the ability to detect mutations, deletions or target regions on a substrate surface, e.g., an electrode surface coated with an insulating self-assembling monolayer and accessible binding ligand. However, if the interfering sequence is present, the masking probe binds to the entire target region so that genotyping is not impacted.

When employed, masking signal probe concentration in signal probe/hybridization buffer should approximate that of individual signal probe species concentration, i.e., be in the range 120 nM to 250 nM, and be accompanied by a buffer solution. GenMark has found that a final signal probe concentration of 1.91 M Guanidine HCL, 37.5 mM MES Hemisodium Salt, 27.2% of a 10% Tween 20 solution, and 1.37 mM 6-Mercapto-1-hexanol works best.

Example 3: Blocking Capture Probes

Blocking capture probes are illustrated with respect to FIGS. 10A-10C. These find utility in ECD schemes where a piece of nucleic acid of interest (target, e.g., PCR amplicon) is too long relative to a single capture probe on a single electrode in a multiplex detection system which is to interrogate multiple different sites within the same target. The blocking probe is complementary to a different portion of the target sequence of interest and helps to keep the other interrogation sites separate and occupied such that they cannot hybridize with complementary signal probes in hybridization complexes on the same electrode surface and thereby supply an interfering background signal. Typically the blocking capture probe sequence will have a stronger or higher affinity for the interfering sequence such that the corresponding signal probe to that sequence is outcompeted kinetically on that particular electrode by the blocking capture probe. One or more other detection electrodes in the multiplex system are, in turn, configured to interrogate the other site(s) that are desired to be excluded from interrogation or background signal contribution on the first electrode.

When employed, blocking capture probe concentration in master spotting solutions (used to spot and dry onto electrodes) may approximate that of regular signal probe concentration, i.e., be 2.5-10 uM, or vary therefrom. For example, GenMark has found 5 uM blocking capture probe and 7.25 uM capture probe to be a useful combination. Such spotting solutions also best include 17 uM CT105, 50 uM TrisHCl, pH 7.4 and RNAse/DNAse free water, or equivalent buffer. CT105 is a disulfide compound that reacts with gold surfaces to yield a mixed self-assembled monolayer (SAM). Its synthesis, structure and reactivity with gold-plated electrode surfaces are described in commonly owned U.S. Pat. No. 6,753,143.

All articles, patents and documents referenced herein, as well as the articles, patents and documents referenced therein, are herein incorporated by reference in there entireties, although the person of ordinary skill already has significant knowledge to appreciate and practice the invention(s) using the guidance herein coupled with no more than routine experimentation.

One skilled in the art will readily appreciate that the present invention(s) is/are well adapted to carry out the objects and obtain the ends and advantages mentioned, as well as those inherent therein.

The methods and compositions described herein illustrate preferred embodiments, are exemplary, and are not intended as limitations on the scope of the invention(s). Certain modifications and other uses will be apparent to those skilled in the art, and are encompassed within the spirit of the invention(s) as defined by the scope of the claims and disclosure herein.

The terms and expressions which have been employed are used as terms of description and not of limitation, and there is no intention in the use of such terms and expressions of excluding any equivalents of the features shown and described, or portions thereof.

It is recognized that various modifications are possible within the scope of the invention(s) disclosed herein. Thus, it should be understood that although the present invention(s) has/have been specifically disclosed by preferred embodiments, optional features, modifications and variations of the concepts herein disclosed may be resorted to by those skilled in the art, and that such modifications and variations are considered to be within the scope as defined by the description and the appended claims.

In addition, where features or aspects of the invention are described in terms of ranges or Markush groups or other grouping of alternatives, e.g., genuses, those skilled in the art will recognize that the invention is also thereby described in terms of any individual measurement, member or subgroup of members of the range, Markush group or subgenus, and exclusions of individual members as appropriate, e.g., by proviso.

We claim:

1. A composition comprising:
   a. a capture binding ligand, the capture binding ligand comprising a first detectable label emitting a first signal at a first potential; and
   b. an analyte bound to a signal binding ligand and the capture binding ligand, the signal binding ligand comprising a second detectable label emitting a second signal at a second potential,
   wherein the first potential and the second potential are different, wherein the capture binding ligand emits the first signal that stays unchanged either in the presence or in the absence of the analyte, and wherein the signal binding ligand emits the second signal only when bound to the analyte.

2. The composition of claim 1, wherein the capture binding ligand is covalently bound to the first detectable label.

3. The composition of claim 1, wherein the first detectable label comprises a redox active label.

4. The composition of claim 3, wherein the redox active label comprises a ferrocene or a ferrocene derivative.

5. The composition of claim 1, wherein the capture binding ligand is bound to a solid support.

6. The composition of claim 5, wherein the solid support comprises an electrode, and wherein the first signal is detected when the electrode is functional.

7. The composition of claim 1, wherein the capture binding ligand comprises a nucleic acid sequence and the signal binding ligand comprises a nucleic acid sequence, and wherein the nucleic acid sequence of the capture binding ligand does not cross-hybridize with the nucleic acid sequence of the signal binding ligand under conditions used to bind the analyte.

8. The composition of claim 1, wherein the analyte comprises a first nucleic acid sequence and a second nucleic acid sequence, wherein the first nucleic acid sequence binds to the capture binding ligand, and wherein the second nucleic acid sequence binds to the signal binding ligand in the same reaction condition.

9. The composition of claim 8, wherein the analyte comprises a third nucleic acid sequence that does not bind to the capture binding ligand or the signal binding ligand.

10. The composition of claim 1, wherein the composition further comprises a surrogate capture probe.

11. A composition comprising:
   a first capture binding ligand bound to a first analyte, the first capture binding ligand comprising a first detectable label emitting a first signal at a first potential,
   wherein the first analyte is bound to a first signal binding ligand, and wherein the first signal binding ligand comprises a second detectable label emitting a second signal at a second potential, wherein the first and second potentials are different, and
   wherein the first capture binding ligand emits the first signal that stays unchanged either in the presence or in the absence of the first analyte and wherein the first signal binding ligand emits the second signal only when bound to the first analyte.

12. The composition of claim 11, the composition further comprising a detector for the first and second signal.

13. The composition of claim 11, further comprising a second capture binding ligand bound to the first analyte, wherein the second capture binding ligand is not bound to a detectable label.

14. The composition of claim 11, wherein the first analyte comprises a first nucleic acid sequence and a second nucleic acid sequence, and
   wherein the composition further comprises a second capture binding ligand, wherein the first capture binding ligand is specific for the first nucleic acid sequence, and wherein the second capture binding ligand is specific for the second nucleic acid sequence.

15. The composition of claim 11, wherein the first analyte comprises a first nucleic acid sequence wherein the first capture binding ligand is specific for the first nucleic acid sequence, and wherein the composition further comprises a second capture binding ligand and a second analyte comprising a second nucleic acid sequence, the second capture binding ligand is specific for the second nucleic acid sequence.

16. The composition of claim 11, wherein the first analyte is an amplicon from a *Bacillus, Vibrio, Escherichia, Shigella, Salmonella, Mycobacterium, M leprae, Clostridium, C. tetani, C. difficile, C. perfringens*, Cornyebacterium, *Streptococcus, S. pyogenes, S. pneurnoniae, Staphylococcus, Haemophilus, Neisseria, N. gonorrhoeae, Yersinia, Pseudomonas, P. putida, Chlamydia, Bordetella,* or *Treponema* microorganism.

17. The composition of claim 11, wherein the first analyte comprises a first nucleic acid sequence and a second nucleic acid sequence, and wherein the composition further comprises a second signal binding ligand, wherein the first signal binding ligand is specific for the first nucleic acid sequence, and the second signal binding ligand is specific for a second nucleic acid sequence.

18. The composition of claim 11, wherein the first analyte comprises a first nucleic acid sequence wherein the first signal binding ligand is specific for the first nucleic acid sequence, and wherein the composition further comprises a second signal binding ligand, a second analyte comprising a second nucleic acid sequence, wherein the second signal binding ligand is specific for the second nucleic acid sequence.

19. A method for detecting a target nucleic acid molecule comprising:
   a. providing a first capture binding ligand, the first capture binding ligand comprising a first detectable label and emitting a first signal at a first potential;
   b. confirming an electrode is functional by detecting the presence of the first signal;
   c. contacting the first capture binding ligand with a sample comprising a target nucleic acid molecule bound to a signal binding ligand, the signal binding ligand comprising a second detectable label, the signal binding ligand emitting a second signal at a second potential wherein the first and second signal are different and wherein the first signal stays unchanged either in the presence or in the absence of the target nucleic acid molecule; and
   d. detecting the presence of the second signal to confirm the presence of the target nucleic acid molecule.

20. The method of claim 19, wherein step (b) comprises measuring a minimum acceptable cut-off signal.

* * * * *

SEQUENCE LISTING

<160> NUMBER OF SEQ ID NOS: 6

<210> SEQ ID NO 1
<211> LENGTH: 5
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(4)
<223> OTHER INFORMATION: Each of nt 1-4 labeled with QW56
<220> FEATURE:
<221> NAME/KEY: misc_feature
<222> LOCATION: (5)..(5)
<223> OTHER INFORMATION: nt 5 labeled with QW56 and QW56-N152

<400> SEQUENCE: 1 ttttt                                                                 5

<210> SEQ ID NO 2
<211> LENGTH: 5
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(4)
<223> OTHER INFORMATION: Each of nt 1-4 labeled with QW80
<220> FEATURE:
<221> NAME/KEY: misc_feature
<222> LOCATION: (5)..(5)
<223> OTHER INFORMATION: nt 5 labeled with QW80 and QW80-N152

<400> SEQUENCE: 2 ttttt                                                                 5

<210> SEQ ID NO 3
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: nt 16 labeled with N152

<400> SEQUENCE: 3
gtcggttccg ctgcag                                                    16

<210> SEQ ID NO 4
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (24)..(24)
<223> OTHER INFORMATION: nt 24 labeled with N152

<400> SEQUENCE: 4
cactttgcac cgtcaggtcc agtg                                           24

<210> SEQ ID NO 5
<211> LENGTH: 28
<212> TYPE: DNA
<213> ORGANISM: Artificial Sequence

```
<220> FEATURE:
<223> OTHER INFORMATION: synthetic
<220> FEATURE:
<221> NAME/KEY: misc_feature
<222> LOCATION: (1)..(5)
<223> OTHER INFORMATION: each of nt 1-5 labeled with QW80

<400> SEQUENCE: 5
ttttcactgg acctgacggt gcaaagtg                                              28

<210> SEQ ID NO 6
<211> LENGTH: 19
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (19)..(19)
<223> OTHER INFORMATION: nt 19 labeled with N152

<400> SEQUENCE: 6
ccaaagtagt cggttccgc                                                        19
```